United States Patent
Sugaya et al.

(10) Patent No.: US 6,635,162 B2
(45) Date of Patent: Oct. 21, 2003

(54) GAS SENSOR

(75) Inventors: Satoshi Sugaya, Nagoya (JP); Norihiko Nadanami, Nagoya (JP); Noboru Ishida, Nagoya (JP); Takafumi Oshima, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/397,931

(22) Filed: Sep. 17, 1999

(65) Prior Publication Data

US 2003/0070924 A1 Apr. 17, 2003

(30) Foreign Application Priority Data

Sep. 17, 1998 (JP) .......................... 10-263109

(51) Int. Cl.[7] ........................................... G01N 27/407
(52) U.S. Cl. ...................... 204/426; 204/425; 205/781
(58) Field of Search ................. 204/421–429; 205/781

(56) References Cited

U.S. PATENT DOCUMENTS

| | | | | |
|---|---|---|---|---|
| 5,672,811 A | * | 9/1997 | Kato et al. ................. 204/425 |
| 5,736,028 A | * | 4/1998 | Hjortsberg et al. ......... 205/781 |
| 5,861,092 A | * | 1/1999 | Kiyota et al. ............... 205/781 |
| 5,877,406 A | | 3/1999 | Kato .......................... 73/23.31 |
| 5,989,624 A | * | 11/1999 | Kida et al. .................. 204/424 |
| 6,019,881 A | * | 2/2000 | Kurosawa et al. .......... 204/426 |
| 6,036,841 A | * | 3/2000 | Kato et al. |
| 6,071,393 A | * | 6/2000 | Oshima et al. ............. 204/426 |
| 6,303,011 B1 | * | 10/2001 | Gao et al. |

OTHER PUBLICATIONS

Nobuhide Kato et al, Thick Film ZrO2 NOx Sensor, 1996, 6 pages.

* cited by examiner

*Primary Examiner*—T. Tung
(74) *Attorney, Agent, or Firm*—Sughrue Mion, PLLC

(57) ABSTRACT

A gas sensor having a laminate structure composed of thin sheets of solid electrolyte and including a cavity portion 21 and an oxygen concentration cell 5. The oxygen concentration in the cavity portion 21 is held constant. The oxygen concentration cell 5 includes an active electrode 12 having a relatively high catalytic capability with respect to NOx or combustible gas and an inner common electrode 13/15 (serving as an inactive electrode and an oxygen-concentration-sensing electrode) having a relatively low catalytic capability with respect to NOx or combustible gas. The oxygen concentration cell 5 is disposed in the gas sensor so as to be exposed to the interior of the cavity portion 21. The concentration of NOx or combustible gas is determined based on an electromotive force (of the order of mV) generated between the active electrode 12 and the inner common electrode 13/15 by a concentration cell effect.

2 Claims, 5 Drawing Sheets

GAS SENSOR

BACKGROUND OF THE INVENTION

1. Field of the Invention

The present invention relates to a gas sensor for measuring the concentration of a gas component such as NOx gas or combustible gas (e.g., HC or CO) in exhaust gas emitted from an internal combustion engine of a vehicle, such as an automobile, ship, or airplane, or from an industrial combustion engine, or in combustion gas emitted from, for example, a boiler.

2. Description of the Related Art

Recently, with exhaust gas regulations being tightened, studies have been conducted on engine control and catalyst control realized through direct measurement of the concentration of NOx, HC, or CO gas in exhaust gas emitted from, for example, an engine. An NOx gas concentration sensor for such an application is disclosed in, for example, SAE paper No. 960334, pp. 137–142, 1996. The NOx gas concentration sensor assumes the form of a laminate of solid electrolyte layers, each formed of a zirconia sheet, and includes a first diffusion passage, a first cavity portion, which communicates with the atmosphere under measurement via the first diffusion passage, a second diffusion passage, and a second cavity portion, which communicates with the first cavity portion via the second diffusion passage. The sensor further includes a first oxygen pump cell and an oxygen sensor cell, which is exposed to the interior of the first cavity portion, and a second oxygen pump cell, which is exposed to the interior of the second cavity portion. The oxygen sensor cell is adapted to measure oxygen concentration in the first cavity portion. On the basis of the measured oxygen concentration, the first oxygen pump cell pumps out oxygen from the first cavity portion, thereby diffusing a gas having a controlled oxygen concentration into the second cavity. A predetermined voltage is applied to a pair of electrodes of the second oxygen pump cell, causing NOx to dissociate into ions on one of the paired electrodes that is exposed to the interior of the second cavity portion. The thus-generated oxygen ions pass through the solid electrolyte that constitutes the second oxygen pump cell. As a result, a limiting current flows between the paired electrodes. On the basis of the limiting current, NOx gas concentration is determined. The paired electrodes of the second oxygen pump cell are disposed such that one electrode is exposed to the interior of the second cavity portion, while the other electrode is exposed to the atmosphere.

According to the above-described conventional gas sensor, oxygen concentration is lowered in the first cavity portion, and the concentration of NOx in the gas diffused into the second cavity portion is determined according to a limiting-current process. Since a detection output (current flowing between the paired electrodes of the second oxygen pump cell) with respect to gas to be measured (hereinafter referred to as "gas under measurement") is very small (of the order of several μA), accurate measurement of such a small current is difficult. In order to detect such a small current, a sensor unit must be of high precision and thus becomes expensive. Also, the structure of the gas sensor becomes complex; specifically, the first and second cavity portions, the first and second oxygen pump cells, and the oxygen sensor cell are provided independently of one another.

SUMMARY OF THE INVENTION

In view of the foregoing, an object of the present invention is to provide a gas sensor that produces a large gas sensor output even with respect to a low-concentration gas to be detected and that has a simple structure.

Aspects of the present invention are described below. First aspect: a cavity portion, whose oxygen concentration is controlled at a constant level; an active electrode having a relatively high catalytic capability with respect to NOx or combustible gas; an inactive electrode having a relatively low catalytic capability with respect to NOx or combustible gas; and an oxygen concentration cell, which is disposed so as to be exposed to the interior of the cavity portion. Second aspect: the active electrode and the inactive electrode are disposed so as to be exposed to the interior of the same cavity portion. Third aspect: the active electrode contains one or more elements from the platinum group, which includes Pt, Rh, Pd, Ir, and Ru; and the inactive electrode contains one or more elements selected from the transition metals, which include Au, Ni, Co, Cr, Fe, Mn, Cu, Ti, and Zn, so that the catalytic capability with respect to NOx or combustible gas becomes lower than that of the active electrode. Fourth aspect: an oxygen-concentration-sensing electrode, which is exposed to the interior of the cavity portion in order to detect oxygen concentration in the cavity portion; an oxygen concentration reference electrode, which generates an electric potential that serves as a reference for the oxygen-concentration-sensing electrode; and the oxygen-concentration-sensing electrode and the inactive electrode are implemented in the form of a common electrode. Fifth aspect: an oxygen-concentration-sensing electrode, which is exposed to the interior of the cavity portion in order to detect oxygen concentration in the cavity portion; an oxygen concentration reference electrode, which generates an electric potential that serves as a reference for the oxygen-concentration-sensing electrode; the oxygen concentration reference electrode and the inactive electrode are implemented in the form of a common electrode; and the common electrode is disposed outside the cavity portion. Sixth aspect: an oxygen-concentration-sensing electrode, which is exposed to the interior of the cavity portion in order to detect oxygen concentration in the cavity portion; an oxygen concentration reference electrode, which generates an electric potential that serves as a reference for the oxygen-concentration-sensing electrode; and the oxygen-concentration-sensing electrode and the active electrode are implemented in the form of a common electrode. Seventh aspect: The cavity portion includes a first cavity portion and a second cavity portion, which communicates with the first cavity portion across a diffusion resistance and to which the oxygen concentration cell is exposed; an oxygen-concentration-sensing electrode, which is exposed to the interior of the first cavity portion in order to detect oxygen concentration in gas that diffuses from the first cavity portion into the second cavity portion; an oxygen concentration reference electrode, which generates an electric potential that serves as a reference for the oxygen-concentration-sensing electrode; an oxygen pump cell, which is exposed to the interior of the first cavity portion and pumps out oxygen from and/or pumps oxygen into the first cavity portion on the basis of the differential in electric potential between the oxygen-concentration-sensing electrode and the oxygen concentration reference electrode; and the active electrode and the inactive electrode are disposed within the second cavity portion. Eighth aspect: NOx or combustible gas concentration is determined by means of the oxygen concentration cell, which is exposed to the interior of the cavity portion whose oxygen concentration is held constant.

Features of preferred embodiments of the present invention will next be described. Preferably, a gas sensor according to the present invention assumes a laminate structure composed of thin sheets of solid electrolyte. An oxygen concentration cell includes an active electrode, an inactive electrode, and an oxygen-ion-conductive solid electrolyte layer on which the active and inactive electrodes are formed. The active and inactive electrodes have a reversible catalytic function (catalytic function related to oxygen dissociation) in relation to at least a dissociation reaction of oxygen molecules for injecting oxygen into the solid electrolyte layer and a recombination reaction of oxygen to cause the solid electrolyte layer to release oxygen. Preferably, in order to hold constant oxygen concentration in a cavity portion, to the interior of which the oxygen concentration cell is exposed, the oxygen pump cell is disposed so as to be exposed to the interior of the cavity portion. By holding the oxygen concentration in the cavity portion constant, the oxygen concentration dependency of an electromotive force (gas sensor output) that is generated by a concentration cell effect in the oxygen concentration cell can be reduced, which oxygen concentration cell is exposed to the interior of the cavity portion. That is, among components of a gas sensor output, an offset corresponding to oxygen concentration (partial pressure of oxygen) in the cavity portion is reduced, thereby reducing variation in gas sensor output caused by temperature variation and abrupt variation in oxygen concentration in the subject gas.

The oxygen pump cell includes an oxygen-ion-conductive solid electrolyte layer and a pair of electrodes formed on the solid electrolyte layer, and is exposed to the interior of the cavity portion to which the oxygen concentration cell is exposed, or to a space that communicates with the cavity portion. The oxygen pump cell is constructed such that upon applying voltage to the paired electrodes, the oxygen pump cell pumps out oxygen from and/or pumps oxygen into the cavity portion or the space communicating with the cavity portion. Preferably, the oxygen pump cell is controlled so as to pump out oxygen according to the difference in electric potential between the oxygen-concentration-sensing electrode, which is exposed to the interior of the cavity portion, and the oxygen concentration reference electrode, which is exposed to an atmosphere of constant oxygen concentration. Specifically, voltage applied to the paired electrodes of the oxygen pump cell is controlled such that the oxygen concentration in the cavity portion attains such a constant, low level as to have substantially no effect on measurement of the concentration of a predetermined gas. In the case of detection of NOx, $NO_2$ may be decomposed in the cavity portion by the oxygen pump cell. Also, a portion of NO may be decomposed in the cavity portion by the oxygen pump cell. The amount of decomposed NO can be compensated by means of, for example, oxygen pump current flowing through the oxygen pump cell.

In order to detect the concentration of NOx gas, the active electrode may contain a reduction catalyst component. The inactive electrode contains a component that suppresses activity of the reduction catalyst component. An electrode component of the inactive electrode may be composed exclusively of a component that suppresses activity of the reduction catalyst component. Also, the active electrode and the inactive electrode may contain a predetermined electrode component and solid electrolyte component in combination. Preferably, a solid electrolyte component carries an electrode component.

In order to detect the concentration of combustible gas (particularly, HC or CO), the active electrode may contain an oxidation catalyst component. The inactive electrode contains a component that suppresses activity of the oxidation catalyst component. That is, the inactive electrode has the function of causing dissociation or recombination of oxygen molecules, and functions to suppress a combining reaction (burning reaction) of a combustible gas component and oxygen. The catalytically active electrode has the function of causing dissociation or recombination of oxygen molecules, and functions as an oxidation catalyst, which accelerates a combining reaction (burning reaction) of a combustible gas component and oxygen. An electrode component of the inactive electrode may be composed exclusively of a component that suppresses activity of the oxidation catalyst component. Also, the active electrode and the inactive electrode may contain a predetermined electrode component and a solid electrolyte component in combination. Preferably, the solid electrolyte component carries an electrode component.

Preferably the active and inactive electrodes are both located in the same cavity and are both exposed to substantially the same atmosphere.

Preferably, the active electrode contains one or more elements selected from the platinum group, which includes Pt, Rh, Pd, Ir and Ru. Preferably, the active electrode further contains Ag. If Ag is added to the platinum group element it increases the activity of the platinum group electrode.

Preferably, the inactive electrode contains one or more of Au, Ni, Co, Cr, Fe, Mn, Cu, Ti and Zn as the element for suppressing the activity of the electrode. In particular, Au or Cu are presently preferred as they work best at making the electrode inactive.

In order to detect NOx gas or combustible gas, the active electrode preferably assumes the form of a porous electrode and contains one or more platinum group elements as a main electrode component, while $ZrO_2$ is added in an amount of approximately 10–20 wt % with respect to the electrode component. The inactive electrode assumes the form of a porous electrode and contains one or more platinum group elements as a main electrode component and approximately 10 wt % transition metal element(s) to suppress catalytic capability of the platinum group element, while $ZrO_2$ is added in an amount of approximately 10–20 wt % with respect to the electrode component. The platinum group element(s) and the transition metal element(s) may be contained in the electrode in the form of an alloy formed of these elements only or an alloy formed of these elements and other components. Particularly, when NOx is to be detected, an element of higher NO dissociation capability (higher catalytic capability), such as Rh, is preferred as a component of the active electrode. When combustible gas is to be detected, the amount of transition metal added to the inactive electrode is preferably increased, since combustible gas is more likely to undergo a catalytic reaction (burning reaction) on the electrodes than in the case of detection of NO. Preferably, when combustible gas is to be detected, voltage applied to the electrodes is lowered, or sensor temperature is lowered.

Preferably, the oxygen-concentration-sensing electrode or the oxygen concentration reference electrode and the inactive or active electrode are implemented in the form of a common electrode, thereby further simplifying gas sensor structure.

The oxygen-concentration-sensing electrode, the oxygen concentration reference electrode, and the electrodes of the oxygen pump cell may be implemented entirely in the form of a Pt porous electrode. This is in order to impart to the electrodes a reversible catalytic function (catalytic function related to oxygen dissociation) in relation to a dissociation reaction of oxygen molecules for injecting oxygen into the solid electrolyte layers on which the electrodes are formed, and a recombination reaction of oxygen to cause the solid electrolyte layers to release oxygen. Preferably, the electrodes are formed such that a portion exposed to the interior of the cavity portion is implemented in the form of an Au porous electrode, while an opposite portion (the other portion) is implemented in the form of a Pt porous electrode. The Au porous electrode is catalytically inactive with respect to reaction of oxygen and a component to be detected, such as methane, while exhibiting a sufficient catalytic function related to oxygen dissociation with respect to operation of the oxygen sensor cell and the oxygen pump cell.

A $ZrO_2$ solid solution containing $Y_2O_3$ or CaO is a typical material for a solid electrolyte layer that constitutes the oxygen sensor cell (having the oxygen-concentration-sensing electrode and the oxygen concentration reference electrode), the oxygen pump cell, and the oxygen concentration cell. Alternatively, the solid electrolyte layer may be formed of a $ZrO_2$ solid solution containing an oxide of an alkaline earth metal or rare-earth metal. $ZrO_2$, which is a base component of the solid electrolyte layer, may contain $HfO_2$. The solid electrolyte layer may contain partially stabilized and/or stabilized $ZrO_2$, $CeO_2$, $HfO_2$, and $ThO_2$. A stabilizer may be selected singly or in combination from the group consisting of, for example, CaO, MgO, and rare-earth oxides (e.g., $Y_2O_3$, $La_2O_3$, and $Gd_2O_3$). Preferably, yttria partially stabilized zirconia powder (YSZ) is used as a stabilizer. Other stabilizers or other solid electrolytes may also be used.

Preferably, the cavity portion is defined between laminated solid electrolyte layers; specifically, between the solid electrolyte layer of the oxygen pump cell and the solid electrolyte layer of the oxygen sensor cell or oxygen concentration cell, and communicates with a subject gas atmosphere through a porous layer that serves as a diffusion passage. The cavity portion may be partially enclosed with an insulating layer. The porous layer that constitutes the diffusion passage reinforces the gas sensor to thereby prevent or suppress warpage or expansion of the gas sensor. Also, by employing the porous layer, contaminant particles, such as soot or oil mist, contained in exhaust gas become unlikely to enter, for example, the cavity portion, thereby preventing or suppressing deterioration of the electrodes, which would otherwise result from adhesion of contaminant particles. Preferably, the porous layer is an alumina-based porous ceramic layer having a number of communication pores formed therein.

In order to lead out outputs from the electrodes, electrode lead portions are formed that extend in the longitudinal direction of the gas sensor toward one end portion (a base end portion at which a sensor element is mounted) and that are electrically connected to the electrodes. The electrode lead portions are connected to leads at the base end portion for external connection. Preferably, the electrode that is in direct contact with a subject gas, such as exhaust gas, is covered with a porous protective film of, for example, alumina, spinel, zirconia, or mullite.

BRIEF DESCRIPTION OF THE DRAWINGS

Specific embodiments of the invention will now be described, by way of example only, with reference to the accompanying drawings in which:

FIG. 1 gives explanatory views showing a gas sensor according to a first embodiment of the present invention, wherein

FIG. 2 gives explanatory views showing a gas sensor according to a first comparative example, wherein

FIG. 3 gives explanatory views showing a gas sensor according to a second embodiment of the present invention, wherein

Figure 1A:
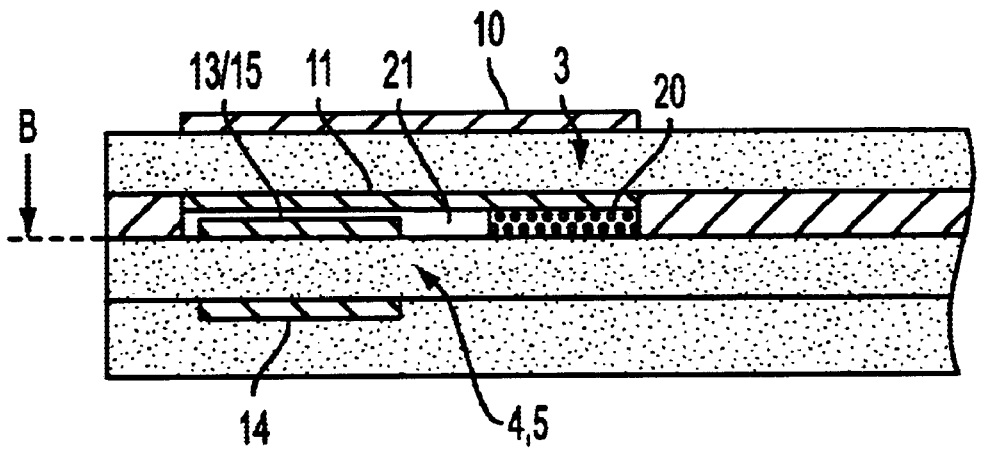
FIG. 1(A) is a longitudinal sectional view of the gas sensor.

Reference numerals are used to label parts in the drawings as follows:

3: oxygen pump cell
4: oxygen sensor cell
5: oxygen concentration cell
10: exterior electrode of oxygen pump cell
11: interior electrode of oxygen pump cell
12: active electrode of oxygen concentration cell
13: inactive electrode of oxygen concentration cell
14: oxygen concentration reference electrode
15: oxygen-concentration-sensing electrode
13/14: outer common electrode (serving as an inactive electrode and an oxygen concentration reference electrode)
13/15: inner common electrode (serving as an inactive electrode and an oxygen-concentration-sensing electrode)
20: diffusion-controlling passage, first diffusion-controlling passage
21: cavity portion, first cavity portion
22: second diffusion-controlling passage
23: second cavity portion

DESCRIPTION OF THE PREFERRED EMBODIMENTS

A gas sensor according to a first embodiment of the present invention shown in FIGS. 1(A) and (B) includes a single cavity portion (detecting space) having a common electrode that serves as the inactive electrode and the oxygen-concentration-sensing electrode. In the gas sensor, a first solid electrolyte layer, which is a component element of an oxygen pump cell 3, and a second solid electrolyte layer, which is a common component element of an oxygen sensor cell 4 and oxygen concentration cell 5, are arranged in layers such that a cavity portion 21 is defined therebetween. In FIG. 1(A), the cavity portion 21 is enclosed by the solid electrolyte layers in the vertical direction and by an insulating layer in the horizontal direction. Diffusion-controlling passages 20 are formed in the same layer as that of the cavity portion 21 at laterally opposite end portions of the gas sensor. The diffusion-controlling passages 20 are exposed to the interior of the cavity portion 21 at positions located away from electrodes 12 and 13/15, thereby establishing communication between a subject gas atmosphere and the cavity portion 21 across a diffusion resistance.

Figure 1B:
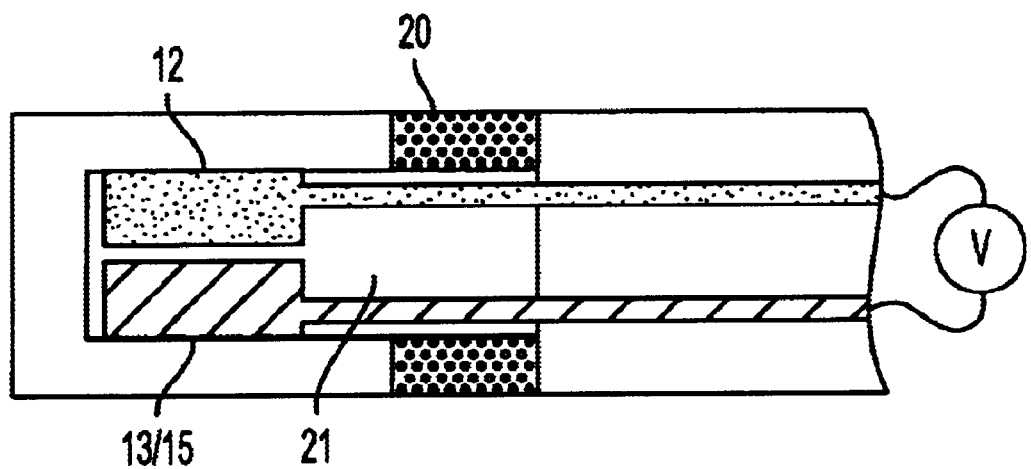
FIG. 1(B) is a plan view as viewed in the direction of arrow B of FIG. 1(A)

Next, the structure of each cell will be described in detail. The oxygen pump cell 3 includes the first solid electrolyte layer, an exterior electrode 10 formed on the first solid electrolyte layer and exposed to the subject gas atmosphere, and an interior electrode 11 formed on the first solid electrolyte layer and exposed to the interior of the cavity portion 21. The oxygen sensor cell 4 includes a second solid electrolyte layer, the inner common electrode 13/15, which is formed on one surface of the second solid electrolyte layer so as to be exposed to the interior of the cavity portion 21 and serves as an oxygen-concentration-sensing electrode and an inactive electrode, and an oxygen concentration reference electrode 14 formed on the other surface of the second solid electrolyte layer and disposed between the second solid electrolyte layer and a third solid electrolyte layer. The oxygen concentration cell 5 includes the second solid electrolyte layer, the active electrode 12 formed on the surface of the second solid electrolyte layer facing the cavity portion 21, and the inner common electrode 13/15, which serves as an inactive electrode and an oxygen-concentration-sensing electrode. As shown in FIG. 1(B), the active electrode 12 and the inner common electrode 13/15 are formed on the same surface of the same solid electrolyte layer.

As shown in FIG. 1(B), leads are connected to the corresponding electrodes 10 to 14 and 13/15 in order to lead out outputs from the electrodes. A heater unit is bonded to the upper or lower surface of the gas sensor by means of a bonding agent (e.g., glass). A resistance-heating element is embedded in a portion of the heater unit that corresponds to the cavity portion 21; i.e., the detecting space, to thereby increase the temperature of the gas sensor, particularly, the temperature of a portion of the gas sensor located in the vicinity of the element (to not lower than 300° C., for example). An unillustrated insulating layer is interposed between the solid electrolyte layers.

Next, a method for controlling the gas sensor will be described. First, an electric circuit is installed that controls voltage applied between the exterior electrode 10 and the interior electrode 11 of the oxygen pump cell 3 according to an electromotive force generated between the oxygen concentration reference electrode 14 and the inner common electrode 13/15 such that the electromotive force becomes constant (a differential amplifier circuit is adapted to apply the voltage between the exterior electrode 10 and the interior electrode 11 such that the electromotive force becomes constant, and a predetermined constant reference voltage is established). A voltmeter is connected between the active electrode 12 and the inner common electrode 13/15 as shown schematically in FIG. 1(B). A small current is supplied to the oxygen concentration reference electrode 14 so that oxygen ions that have been generated through dissociation within the cavity portion 21 are transported to the oxygen concentration reference electrode 14 through the solid electrolyte layer to thereby establish an atmosphere of constant oxygen concentration in the vicinity of the oxygen concentration reference electrode 14. Thus, the oxygen concentration reference electrode 14 serves as a self-generation-type reference electrode.

Next, the operation of the gas sensor will be described. When the gas sensor is exposed to a subject gas, the subject gas diffuses into the cavity portion 21 through the diffusion-controlling passage 20. An electromotive force corresponding to the oxygen concentration in the cavity portion 21 is generated between the inner common electrode 13/15 and the oxygen concentration reference electrode 14. The pumping out of oxygen effected by the oxygen pump cell 3 is controlled according to the thus-generated electromotive force, thereby maintaining oxygen concentration in the cavity portion 21 at a constant level.

When NOx gas is measured, the oxygen concentration as measured in the vicinity of the inner common electrode 13/15 becomes lower than that measured in the vicinity of the active electrode 12. Thus, an electromotive force corresponding to an NOx gas concentration to be measured is generated between the active electrode 12 and the inner common electrode 13/15, which constitute the oxygen concentration cell 5, by a concentration cell effect, while the active electrode 12 is of positive polarity.

When a combustible gas is measured, the amount of oxidation-induced consumption of combustible gas measured in the vicinity of the active electrode 12 becomes greater than that measured in the vicinity of the inner common electrode 13/15. Accordingly, the amount of oxygen consumption measured in the vicinity of the active electrode 12 becomes greater than that measured in the vicinity of the inner common electrode 13/15. Thus, oxygen concentration measured in the vicinity of the inner common electrode 13/15 becomes higher than that measured in the vicinity of the active electrode 12. As a result, an electromotive force corresponding to the combustible gas concentration to be measured is generated between the active electrode 12 and the inner common electrode 13/15 by a concentration cell effect, while the inner common electrode 13/15 is of positive polarity.

Figure 2A:
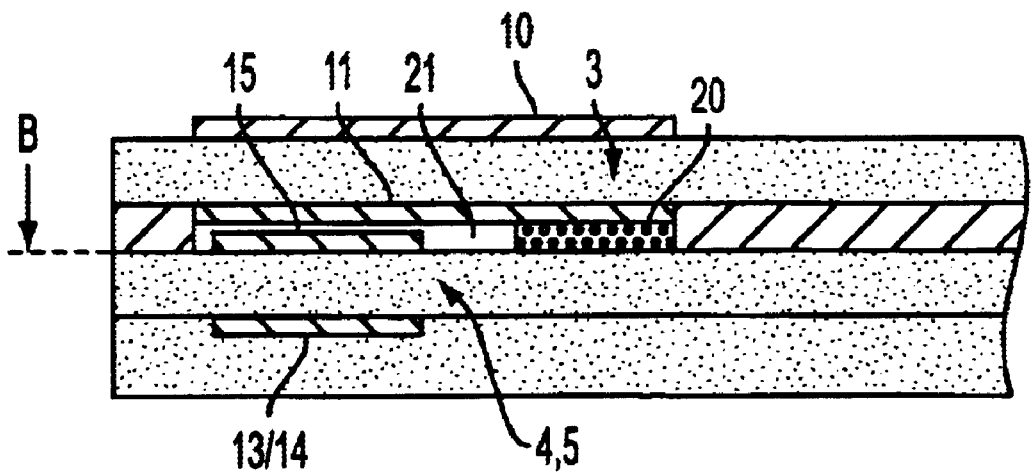
FIG. 2(A) is a longitudinal sectional view of the gas sensor.

A gas sensor according to a first comparative example shown in FIGS. 2(A) and (B) is characterized in that the inactive electrode and the oxygen concentration reference electrode are implemented in the form of a common electrode (the common electrode is represented by an "outer common electrode 13/14"). According to this configuration, on the basis of an electromotive force generated between an oxygen-concentration-sensing electrode 15 and the outer common electrode 13/14, the oxygen pump cell 3 pumps out oxygen from the cavity portion 21, thereby holding constant the oxygen concentration in the cavity portion 21. The concentration of gas to be measured is determined on the basis of an electromotive force that is generated between the active electrode 12 and the outer common electrode 13/14 by a concentration cell effect. Preferably a small current flows between the oxygen-concentration-sensing electrode 15 and the outer common electrode 13/14 so that the outer common electrode 13/14 serves as a self-generation-type reference electrode. Other features are similar to those of the above-described first embodiment.

Figure 3A:
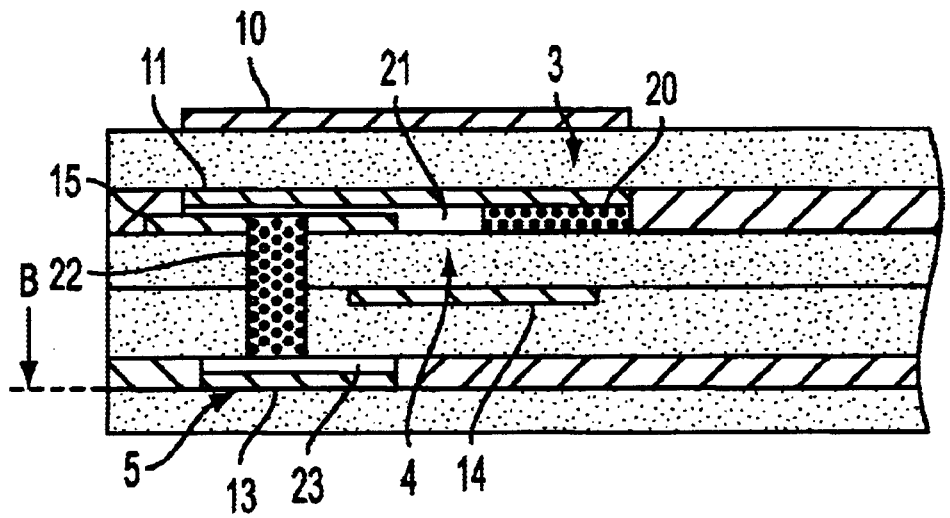
FIG. 3(A) is a longitudinal sectional view of the gas sensor.

A gas sensor according to a second embodiment of the present invention shown in FIGS. 3(A) and (B) is characterized in that two cavity portions are provided, and the oxygen sensor cell and the oxygen concentration cell are formed on different layers. Specifically, the gas sensor includes, from top to bottom in FIG. 3(A), an oxygen pump cell 3 that includes a first solid electrolyte layer and paired electrodes 10 and 11 formed on opposite sides of the first solid electrolyte layer, an insulating layer that surrounds a first cavity portion 21 horizontally in FIG. 3(A), an oxygen sensor cell 4 that includes a second solid electrolyte layer and paired oxygen concentration reference electrode 14 and oxygen-concentration-sensing electrode 15 formed on opposite sides of the second solid electrolyte layer, a third electrolyte layer serving as a support cell, an insulating layer that surrounds a second cavity portion 23 horizontally in FIG. 3(A), and an oxygen concentration cell 5 that includes a fourth solid electrolyte and electrodes 12 and 13 formed on the same side of the fourth solid electrolyte layer. An insulating layer is interposed between the solid electrolyte layers. The first cavity portion 21 is defined between the oxygen pump cell 3 and the oxygen sensor cell 4 by means of the lateral insulating layer shown in FIG. 3(A) and the upper and lower solid electrolyte layers shown in FIG. 3(A).

Similarly, the second cavity portion 23 is defined above the oxygen concentration cell 5 by means of the insulating layer and the solid electrolyte layers. First diffusion-controlling passages 20 are formed at laterally opposite end portions of the gas sensor so as to be exposed to the interior of the first cavity portion 21 at one end, to thereby establish communication between a subject gas atmosphere and the first cavity portion 21 across a diffusion resistance. A second diffusion-controlling passage 22 is disposed away from the first diffusion-controlling passages 20 so as to be exposed to the interior of the first cavity portion 21 at the other end, to thereby establish communication between the first and second cavity portions 21 and 23 across a diffusion resistance. According to this gas sensor, the oxygen pump cell 3 pumps out oxygen from and/or pumps oxygen into the first cavity portion 21 based on the output of the oxygen sensor cell 4, which is exposed to the interior of the first cavity portion 21, thereby holding constant the concentration of oxygen in gas diffusing into the second cavity portion 23. The concentration of gas to be measured is determined by means of the oxygen concentration cell 5, which is exposed to the interior of the second cavity portion 23. Preferably, the oxygen concentration reference electrode 14 serves as a self-generation-type reference electrode as in the case of embodiment 1.

Figure 3B:
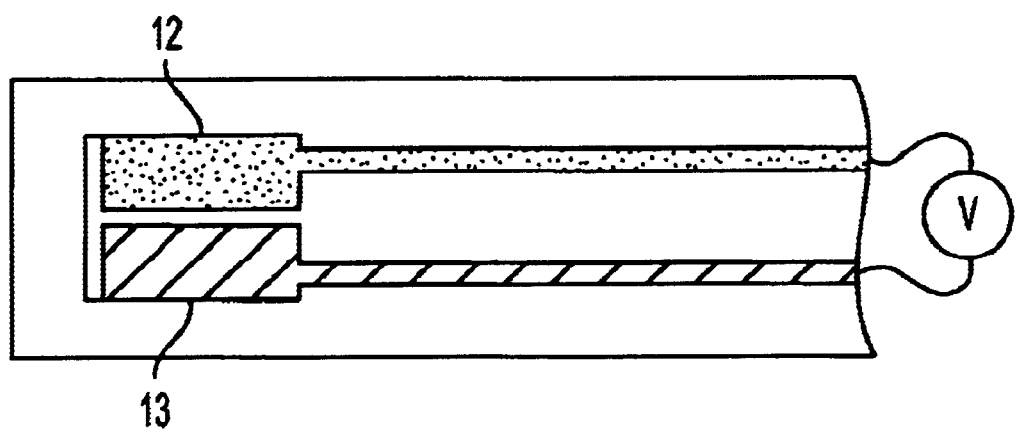
FIG. 3(B) is a plan view as viewed in the direction of arrow B of FIG. 3(A)

In the gas sensor according to the second embodiment, an active electrode 12 and an inactive electrode 13 are formed on the solid electrolyte layer that constitutes the oxygen concentration cell 5, on the same surface exposed to the interior of the second cavity portion 23. The voltage difference between the active electrode 12 and the inactive electrode 13 of the oxygen concentration cell 5 is measured by a voltmeter as shown schematically in FIG. 3(B). According to this configuration, a pair of electrodes 12, 13 of the oxygen concentration cell 5 may be formed on a single side of the solid electrolyte layer, thereby simplifying the structure of the oxygen concentration cell and reducing man-hours of manufacture as compared to the case where the electrodes are formed on opposite sides of the solid electrolyte layer. Other features are similar to those of the gas sensor according to the above-described first embodiment. Also, in yet another embodiment, the active electrode of the oxygen concentration cell and the oxygen-concentration-sensing electrode may be implemented in the form of a common electrode.

According to the preferred embodiments of the invention, the active and inactive electrodes of the concentration cell which produce an electromotive force for sensing gas are both located in the same cavity and are both exposed to substantially the same atmosphere.

Next will be described a preferred process for manufacturing an NOx gas concentration sensor according to an embodiment of the present invention. The sensor is fabricated by laminating, for example, $ZrO_2$ green sheets and electrode pastes and firing the resultant laminate. Paste materials for insulating coat and electrodes are screen-printed on predetermined $ZrO_2$ green sheets (which will become solid electrolyte layers of the oxygen pump cell, oxygen sensor cell, and oxygen concentration cell), thereby forming insulating layers and electrodes at predetermined positions in a laminate. Processes for manufacturing the $ZrO_2$ green sheet and other elements are described below.

Fabrication of $ZrO_2$ Green Sheet:

$ZrO_2$ powder is preliminarily fired in an atmospheric furnace. The preliminarily fired $ZrO_2$ powder, a dispersant, an organic solvent, and balls are mixed and dispersed. To the resulting mixture, an organic binder dissolved in an organic solvent is added, followed by mixing to thereby obtain a slurry. The thus-obtained slurry is sheeted according to a doctor blading method, yielding a $ZrO_2$ green sheet having a thickness of approximately 0.4 mm.

Pastes for Use in Printing:

(1) Paste for use in printing the exterior electrode 10 of the oxygen pump cell, the oxygen concentration reference electrode 14, and the interior and exterior electrodes of a second oxygen pump cell 50 (in a comparative example that will be described later): Platinum powder, $ZrO_2$ powder, and an appropriate amount of an organic solvent are mixed and dispersed. To the resulting mixture, an organic binder dissolved in an organic solvent is added, and a viscosity conditioner is further added, followed by mixing to thereby yield a paste.

(2) Paste for use in printing interior electrode 11 of oxygen pump cell and oxygen-concentration-sensing electrode 15: Platinum powder, $ZrO_2$ powder, gold powder, and an appropriate amount of organic solvent are mixed and dispersed. To the resulting mixture, an organic binder dissolved in an organic solvent is added, and a viscosity conditioner is further added, followed by mixing to thereby yield a paste. Alternatively, $ZrO_2$ powder is impregnated with an Au solution (e.g., a gold chloride solution), followed by drying and firing to thereby cause Au to adhere to the powder. Thus, an Au-carrying powder is obtained. The thus-obtained Au-carrying powder and Pt powder are mixed. To the resulting mixture, a binder, an organic solvent, and a viscosity conditioner are added as appropriate, yielding a paste.

(3) Paste for use in printing insulating coat and protective coat: Alumina powder and an appropriate amount of an organic solvent are mixed and dissolved. To the resulting mixture, a viscosity conditioner is added, followed by mixing to thereby yield a paste.

(4) Paste for use in printing Pt-containing porous material (leads): Alumina powder, platinum powder, an organic binder, and an organic solvent are mixed. To the resulting mixture, a viscosity conditioner is added, followed by mixing to thereby yield a paste.

(5) Paste for use in printing diffusion resistance element: Alumina powder, an organic binder, and an organic solvent are mixed and dispersed. To the resulting mixture, a viscosity conditioner is added, followed by mixing to thereby yield a paste.

(6) Paste for use in printing carbon coat: Carbon powder, an organic binder, and an organic solvent are mixed and dispersed. To the resulting mixture, a viscosity conditioner is added, followed by mixing to thereby yield a paste. By forming a carbon coat layer by printing, electrical contact between electrodes, for example, can be prevented. The carbon coat is also used in a process for forming an internal cavity. Because carbon burns out during firing, a carbon coat layer is not present in a fired body.

(7) Paste for use in printing active electrode of oxygen concentration cell (Pt electrode): Platinum powder, $ZrO_2$ powder, and an appropriate amount of an organic solvent are mixed and dispersed. To the resulting mixture, an organic binder dissolved in an organic solvent is added, and a viscosity conditioner is further added, followed by mixing to thereby yield a paste.

(8) Paste for use in printing inactive electrode of oxygen concentration cell, outer common electrode 13/14, and inner common electrode 13/15 (Au-Pt electrode): Platinum powder, $ZrO_2$ powder, gold powder, and an appropriate amount of an organic solvent are mixed and dispersed. To the resulting mixture, an organic binder dissolved in an organic solvent is added, and a viscosity conditioner is further added, followed by mixing to thereby yield a paste. Alternatively, $ZrO_2$ powder is impregnated with an Au solution (e.g., a gold chloride solution), followed by drying and firing to thereby cause Au to adhere to the powder. Thus, an Au-carrying powder is obtained. The thus-obtained Au-carrying powder and Pt powder are mixed. To the resulting mixture, a binder, an organic solvent, and a viscosity conditioner are added as appropriate, yielding a paste. In this case, $ZrO_2$ particles carry Au, so that Au is finely dispersed to thereby lower interface resistance.

Lamination of $ZrO_2$ Green Sheets, Removal of Binder, and Firing:

$ZrO_2$ green sheets, each printed with an element by use of a predetermined paste, are laminated and compression-bonded. The resulting laminate is subjected to binder removal and firing.

EXAMPLES

The present invention is further described by way of way of the following Examples which should not be construed as limiting the invention.

Example 1

A heater element was bonded to a gas sensor having a structure according to the first embodiment of the present invention shown in FIG. 1. Voltage was applied to the oxygen pump cell such that an electromotive force generated in the oxygen sensor cell assumed a constant value of 350 mV. The gas sensor output (an electromotive force generated between the paired electrodes of the oxygen concentration cell by a concentration cell effect) was measured while the NO concentration of the gas exposed to the gas sensor was varied.

In the case of the gas sensor of Example 1 (see FIG. 1), a Pt electrode ($ZrO_2$ was added in an amount of 14% with respect to an electrode component) was used as the active electrode 12 of the oxygen concentration cell, and an Au1.5%-Pt electrode ($ZrO_2$ was added in an amount of 14% with respect to an electrode component) was used as the inner common electrode 13/15, which served as the inactive electrode and the oxygen-concentration-sensing electrode.

Comparative Example 1

Figure 2B:
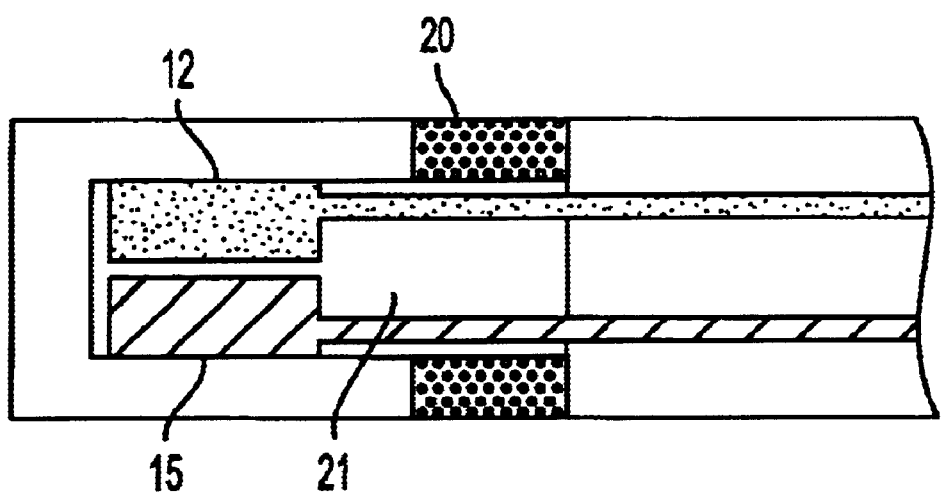
FIG. 2(B) is a plan view as viewed in the direction of arrow B of FIG. 2(A)

Using a gas sensor having a structure according to the first comparative example shown in FIG. 2, measurement was carried out in a manner similar to that of the above-described Example 1. In the case of the gas sensor of example 2 (see FIG. 2), an Rh8%-Pt electrode ($ZrO_2$ was added in an amount of 14% with respect to an electrode component) was used as the active electrode 12; an Au1.5%-Pt electrode ($ZrO_2$ was added in an amount of 14% with respect to an electrode component) was used as the outer common electrode 13/14, which served as the inactive electrode and the oxygen concentration reference electrode; and a platinum electrode ($ZrO_2$ was added in an amount of 10% with respect to an electrode component) was used as the oxygen-concentration-sensing electrode 15.

The electrodes were fabricated according to the method described above in the "Embodiments" section. In the above-described Examples, the oxygen concentration reference electrode 14 and the outer common electrode 13/14 served as a self-generation-type reference electrode. Conditions of measurement in the Examples were as follows. Subject gas composition: NO concentration=0–1500 ppm; $CO_2$ concentration=10%; $H_2O$ concentration=10%; $O_2$ concentration=7%; $N_2$ concentration=balance. Gas temperature: 300° C. Temperature of sensing element of gas sensor: 800° C.

Comparative Example 2

Figure 4:
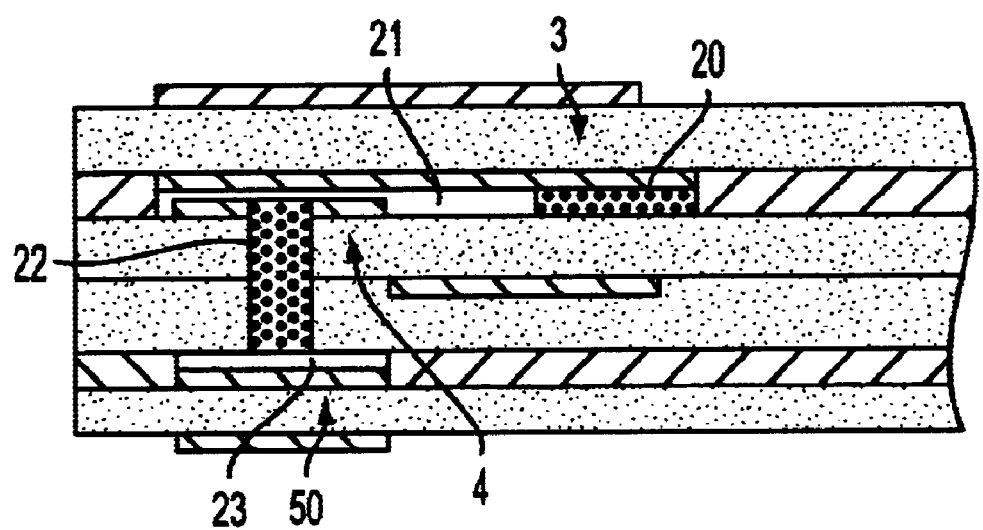
FIG. 4 is a longitudinal sectional view of an NOx gas sensor according to a second comparative example.

A gas sensor having a structure shown in FIG. 4 was fabricated as another comparative example according to the method described above in the "Embodiments" section. Using the gas sensor, measurement was carried out in a manner similar to that described above. Referring to FIG. 4, the gas sensor of Comparative Example 2 assumed the form of a laminate of four solid electrolyte layers while an insulating layer was interposed between the solid electrolyte layers. Specifically, the first solid electrolyte layer constitutes a first oxygen pump cell 3; the second solid electrolyte layer constitutes an oxygen sensor cell 4; the third solid electrolyte layer constitutes a support cell; and the fourth solid electrolyte layer constitutes a second oxygen pump cell 50. A first cavity portion 21 is defined between the first oxygen pump cell 3 and the oxygen sensor cell 4. A second cavity portion 23 is defined between the support cell and the second oxygen pump cell 50. An exterior atmosphere communicates with the first cavity portion 21 through a first diffusion-controlling passage 20, which is formed of a porous insulator. A second diffusion-controlling passage 22, which is formed of a porous insulator, extends between the first cavity portion 21 and the second cavity portion 23 in the direction of lamination to thereby establish communication between the first and second cavity portions 21 and 23. In the gas sensor of the Comparative Example, the first oxygen pump cell 3 is controlled based on an electromotive force that is generated between a pair of electrodes of the oxygen sensor cell 4 in proportion to oxygen concentration in the first cavity portion 21, so that gas whose oxygen concentration is held at a constant low level diffuses into the second cavity portion 22. A constant voltage is applied between a pair of electrodes (Pt electrodes ($ZrO_2$ is added in an amount of 14% with respect to an electrode component)) of the second oxygen pump cell 50. Current induced by oxygen ions generated by dissociation of NO and which flows between the paired electrodes is measured as a gas sensor output.

Results of Measurements—Example 1 and 2 and Comparative Example 1

Figure 5:
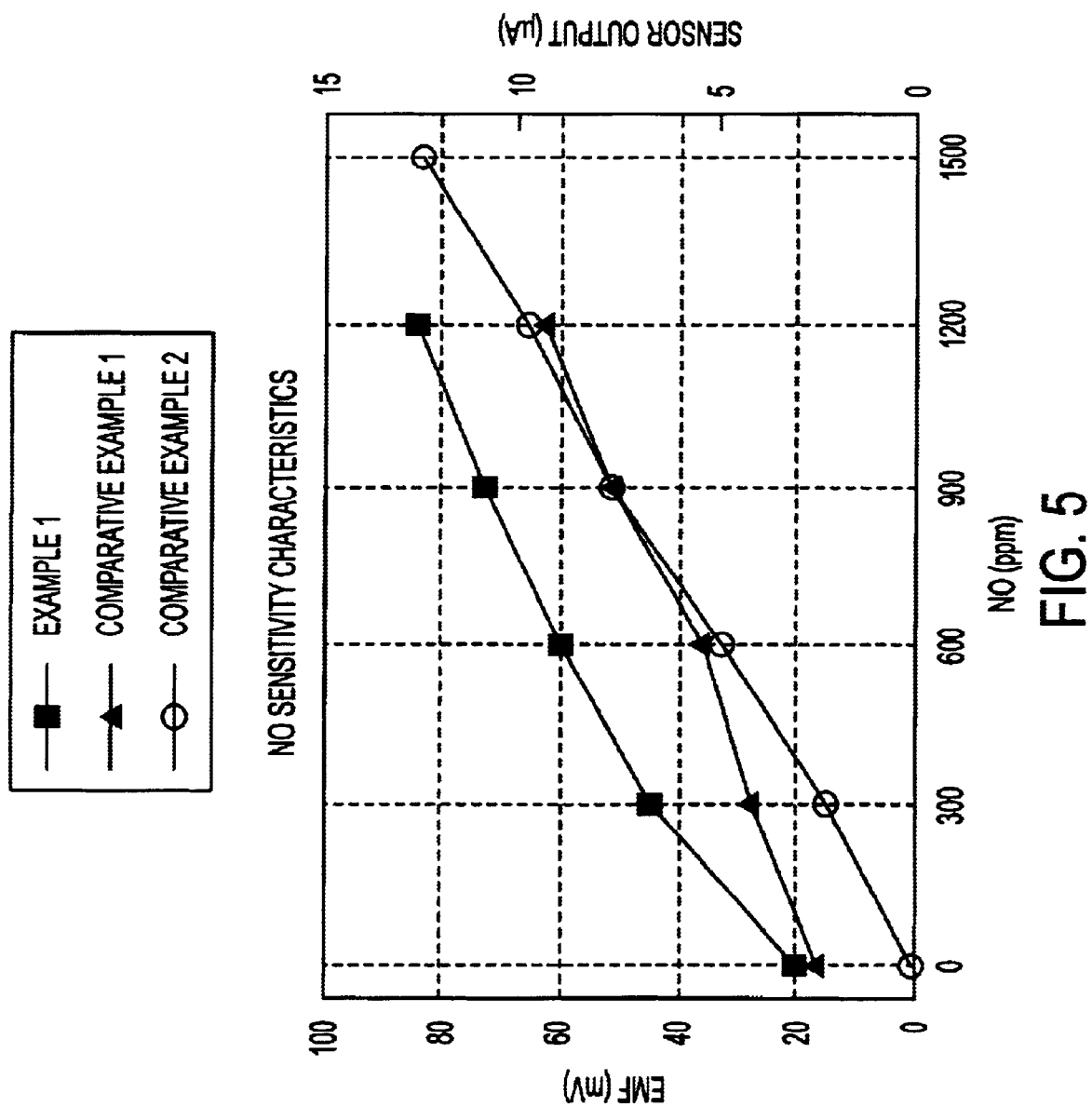
FIG. 5 is a graph of the results of measuring NO concentration by use of the gas sensors according to the first embodiment and the first and second comparative examples.

FIG. 5 is a graph showing the results of measurement in Examples 1 and 2 and Comparative Example 1. FIG. 5 shows the relationship between NO concentration of the gas exposed to the gas sensor and electromotive force, EMF (mV), generated by the concentration cell effect in the case of Example 1 and Example 2, and the relationship between NO concentration of the gas exposed to the gas sensor and oxygen pump current ($\mu A$) flowing through the second oxygen pump cell in the case of Comparative Example 1. As seen from FIG. 5, in the case of Example 1 and Example 2, the gas sensor output EMiF varies substantially linearly with NO concentration, indicating that NO gas concentration can be accurately determined by means of the oxygen concentration cell. Further, since, in the case of Example 1 and Example 2, the electromotive force EMF that the gas sensor generates is on the order of mV, the output from the gas sensor can be detected more easily than in the case of Comparative Example 1, in which NO gas concentration is determined based on a current that is on the order of μA. Also, an inexpensive sensing apparatus of relatively low precision can be employed. Particularly, the gas sensor of Examples 1 and 2 exhibit a large increment in electromotive force per ppm in NO concentration $\{(85-20)/(1200-0)= 0.054\ [mV/ppm]\}$.

A gas sensor according to the present invention outputs a high level of voltage (i.e., mV order) across the inactive and active electrodes placed on the same surface of the electrolyte and exposed to substantially the same atmosphere inside the same cavity. This is because a concentration cell effect is caused along the electrolyte between these electrodes. Therefore, a high degree of accuracy in detecting a low concentration of a gas component below 100 ppm can be attained easily based on such mV order voltage, as compared to a conventional current based measurement. The concentration of various kinds of gas components can be detected using a gas sensor having the same mechanical structure by adjusting the composition of the oxygen concentration cell electrode according to the gas to be detected; thus, production efficiency becomes high.

The invention has been described in terms of measuring the concentration of a particular component in a gas based on the voltage measured between the active and inactive electrodes, as shown in the sensitivity characteristic in FIG. 5. However, application of the invention is not limited to this measurement. The voltage that appears across the active and inactive electrodes can fluctuate depending on the kind of gas mixture entering the cavity as well as the concentration of the gas component being sensed. For example, suppose that the gas contains a constant NOx amount and the proportions of other gas components are also constant. In this state, the measured voltage shows a particular constant value. If an HC gas component is introduced into the gas, then the voltage value instantly changes to a lower level which can be down to zero or even negative. This is because the NOx dissociates at the active electrode producing oxygen, while the HC gas oxidizes and depletes the oxygen on the active electrode. This voltage variation means that the content of the gas being measured has changed. In this way the voltage variation can be used as an indicator of gas-content variation. Thus, the gas sensor can be used to detect a change in the conditions of an engine emitting the exhaust gas being measured as well as, or instead of, measuring the concentration of a particular gas component in the exhaust gas.

While the invention has been described in detail and with reference to specific embodiments thereof, it will be apparent to one skilled in the art that various changes and modifications can be made therein without departing from the spirit and scope thereof.

What is claimed is:

1. A gas sensor, comprising:

a solid electrolyte layer;

a common oxygen reference electrode formed on a first side of the solid electrolyte layer and embedded within said sensor;

two oxygen concentration electrodes formed side by side on a second side of the solid electrolyte layer such that both oxygen concentration electrodes are opposed to the common reference electrode;

a common cavity formed over the two oxygen concentration electrodes, said two oxygen concentration electrodes being exposed to the common cavity so as to be in contact with the same gas atmosphere;

means for measuring the concentration of NO, comprising means for detecting a voltage across the two oxygen concentration electrodes; and means for establishing an atmosphere of constant oxygen concentration in the vicinity of the embedded common oxygen reference electrode;

wherein one of the oxygen concentration electrodes is an active electrode containing Pt, and the other oxygen concentration electrode is an inactive electrode containing Pt and Au, said gas sensor further comprising means for measuring electric potential between the inactive electrode and the common oxygen reference electrode, and said sensor outputting a voltage across the two oxygen concentration electrodes which varies substantially linearly with NO concentration.

2. The gas sensor as claimed in claim 1, further comprising a second solid electrolyte layer forming the cavity together with said solid electrolyte layer and having two electrodes sandwiching the second solid electrolyte layer forming an oxygen pumping cell.

* * * * *